(12) United States Patent
Tigwell

(10) Patent No.: US 7,498,807 B2
(45) Date of Patent: Mar. 3, 2009

(54) PATIENT TABLE

(75) Inventor: Neil Charles Tigwell, Witney (GB)

(73) Assignee: Siemens Magnet Technology, Ltd., Witney (GB)

( * ) Notice: Subject to any disclaimer, the term of this patent is extended or adjusted under 35 U.S.C. 154(b) by 146 days.

(21) Appl. No.: 11/594,166

(22) Filed: Nov. 8, 2006

(65) Prior Publication Data

US 2008/0127416 A1     Jun. 5, 2008

(30) Foreign Application Priority Data

Nov. 11, 2005   (GB)   ................. 0523026.3

(51) Int. Cl.
*G01V 3/00* (2006.01)
(52) U.S. Cl. .................. 324/307; 324/309
(58) Field of Classification Search ......... 324/300–322; 600/407–422
See application file for complete search history.

(56) References Cited

U.S. PATENT DOCUMENTS

| | | | | |
|---|---|---|---|---|
| 3,832,980 A | * | 9/1974 | Fujikawa et al. | 123/200 |
| 4,629,989 A | * | 12/1986 | Riehl et al. | 324/318 |
| 5,579,728 A | * | 12/1996 | Gotmalm | 123/41.55 |
| 6,385,481 B2 | | 5/2002 | Nose et al. | |
| 6,909,283 B2 | * | 6/2005 | Emeric et al. | 324/300 |
| 7,026,815 B2 | * | 4/2006 | Harvey et al. | 324/318 |
| 7,135,863 B2 | * | 11/2006 | Arik et al. | 324/318 |
| 7,215,231 B1 | * | 5/2007 | Morrone | 335/299 |
| 2002/0148604 A1 | | 10/2002 | Emeric et al. | |
| 2008/0023666 A1 | * | 1/2008 | Gurin | 252/74 |

FOREIGN PATENT DOCUMENTS

| | | |
|---|---|---|
| EP | 0 931 505 A2 | 7/1999 |
| EP | 1 066 792 A1 * | 6/2000 |
| GB | 1059740 | 2/1967 |
| JP | 9-98969 A | 4/1997 |

OTHER PUBLICATIONS

Great Britain Search Report dated Mar. 30, 2006 (One (1) page).

* cited by examiner

*Primary Examiner*—Brij B Shrivastav
(74) *Attorney, Agent, or Firm*—Crowell & Moring LLP

(57) ABSTRACT

A patient table for use in equipment such as Magnetic Resonance Imaging (MRI) scanners that are susceptible to electrical or magnetic interference, is moved by hydraulic means, thus avoiding the need for electric motors that give rise to such interference.

7 Claims, 2 Drawing Sheets

PATIENT TABLE

BACKGROUND OF THE INVENTION

The invention is concerned with patient tables which need to be moved horizontally or vertically during treatment or investigation.

Such tables may be found, for example, in scanning equipment such as Magnetic Resonance Imaging (MRI) equipment where typically, a patient needs to be raised or lowered to a correct height and moved into the field of influence of a superconducting magnet. Existing patient tables are moved by means of electric motors mechanically coupled to the table by systems such as lead screws. Problems arise with this arrangement due to interaction between the magnetic/electric fields associated with the motor and the scanning equipment. In order to operate, the motors have to be situated in areas of low magnetic field or be heavily shielded. Also, the motors cause electrical noise which can interfere with the scanners electrical systems. This is a particular problem if the table is moved during the scanning sequence.

Other equipment such as patient cooling fans and solenoid operated switches give rise to similar problems of interaction with electric motors. Existing equipment such as MRI scanners employ cryogenic refrigeration means to maintain the temperature of the superconducting magnet at a value below which quenching occurs. (This is a process in which the magnet undergoes a transition to a normal conducting state). The valves used to control the delivery and return of cryogenic refrigerant are typically electrically operated and hence provide another source of unwanted interference with the scanning equipment.

Applicant's co-pending United Kingdom Patent Application number GB0520389.8 describes a cryogenic refrigerator comprising a rotary valve which controls the flow of high pressure gas into the refrigerator and the return of the gas from the refrigerator, wherein a rotary fluid motor is arranged to drive the rotary valve.

MRI scanners also include a gradient coil, which is effectively a tube of resin with electrical coil windings and cooling tubes embedded into it. Temperature control is assisted by pumping cooling fluid around the gradient coil. The pressure drop across the gradient coil in these systems is typically 2 Bar. Hence existing equipment designs include plumbing arrangements able to deliver fluid to the vicinity of the equipment and able to cope with such fluid pressures.

The present invention is directed, which may be, for example, a Magnetic Resonance Imaging (MRI) scanner having a gradient coil, with the fluid being directed to the vicinity of said gradient coil. The apparatus may also include means for preventing flow of fluid to the gradient coil while the hydraulic pistons or motors are operated, as well as means for directing fluid to other components of the apparatus, for example a hydraulic motor arranged to drive a patient cooling fan or cryogenic fluid delivery valves.

The invention is also directed towards a method of operating the apparatus such as an MRI scanner, the method comprising the step of cooling a gradient coil by directing the fluid thereto. The flow of fluid to the gradient coil may be prevented during the step of moving the table and fluid could be directed to other components of the MRI scanner such as a hydraulic motor arranged to drive a patient cooling fan or cryogenic fluid delivery valves.

The invention uses hydraulic pistons (cylinders) or motors to provide the motive force necessary to move a component such as a patient table. Thus, the problems of interference between the electric motors and the electrical scanning equipment are avoided. Moreover, use of a single fluid for both cooling and hydraulics reduces the additional space and reworking of existing designs necessary, which in turn provides a cost benefit.

A major advantage of the invention is that it can be produced through upgrading of existing systems. Thus an existing apparatus having a cooling system which directs coolant fluid to components of the system, and also employs motors (e.g., electric motors) for moving components, can be upgraded by replacing the motors with a hydraulic piston or motor; modifying the coolant fluid conduits so that fluid is also directed to the hydraulic piston or motor and employing a fluid suitable for acting as coolant and hydraulic fluid in the system.

Other objects, advantages and novel features of the present invention will become apparent from the following detailed description of the invention when considered in conjunction with the accompanying drawings.

DETAILED DESCRIPTION OF THE DRAWINGS

Figure 1:
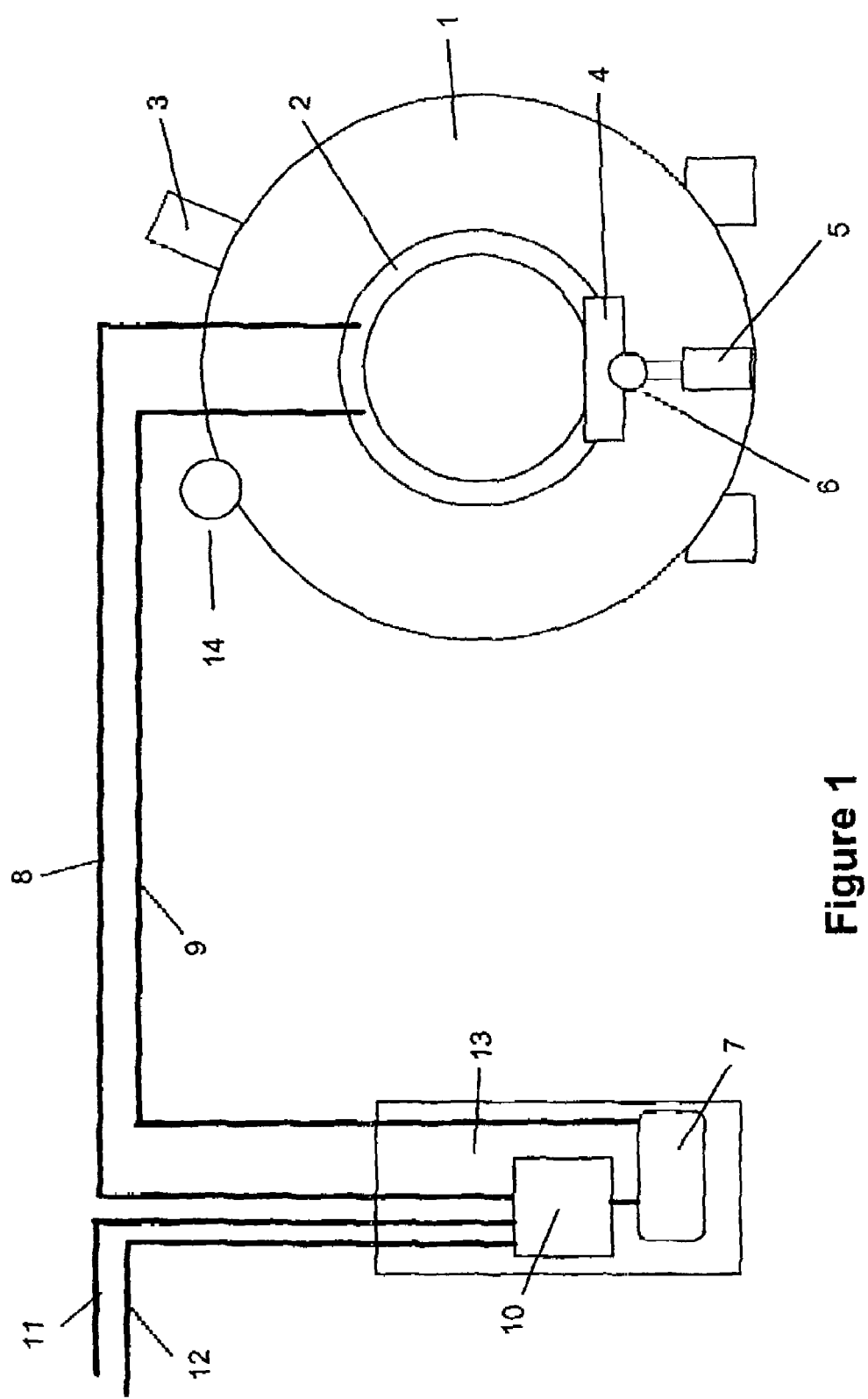
FIG. 1 shows a schematic representation of an MRI scanner typically found in the prior art.

Referring to FIG. 1, a typical MRI scanner of the prior art comprises a superconducting scanning magnet 1, and a gradient coil 2 used to generate a magnetic field gradient. Gradient coil 2 comprises windings of material which is maintained at about 20° C. during operation. During the scanning operation, a patient rests on patient table 4 which is then moved into the bore of the scanning magnet/gradient coil 1 and 2. Vertical and horizontal movement of the patient table are provided by electric motors 5 and 6 respectively.

Cooling of the gradient coil 2 is achieved by delivery of cooling fluid such as water to a matrix of conduits (not shown) in close proximity with the coil 2 such that heat passes from the coil 2 to the coolant. A coolant flow circuit is formed by a pump 7, a secondary supply conduit 8, the matrix of conduits in the coil 2 and a secondary return conduit 9. The secondary coolant flow path passes through a heat exchanger 10 where heat passes from the secondary coolant to chilled primary coolant delivered to the heat exchanger by primary coolant supply conduit 11. The primary coolant then leaves heat exchanger 10 via primary coolant return conduit 12. Pump 7 and heat exchanger 10 would typically be enclosed in a cooler cabinet 13, while an electric fan 14 provides cooling for the patient.

In a system such as illustrated by FIG. 1, problems arise, as described previously, due to electrical/magnetic interference between (inter alia) electric motors 5, 6 and the scanning equipment.

Figure 2:
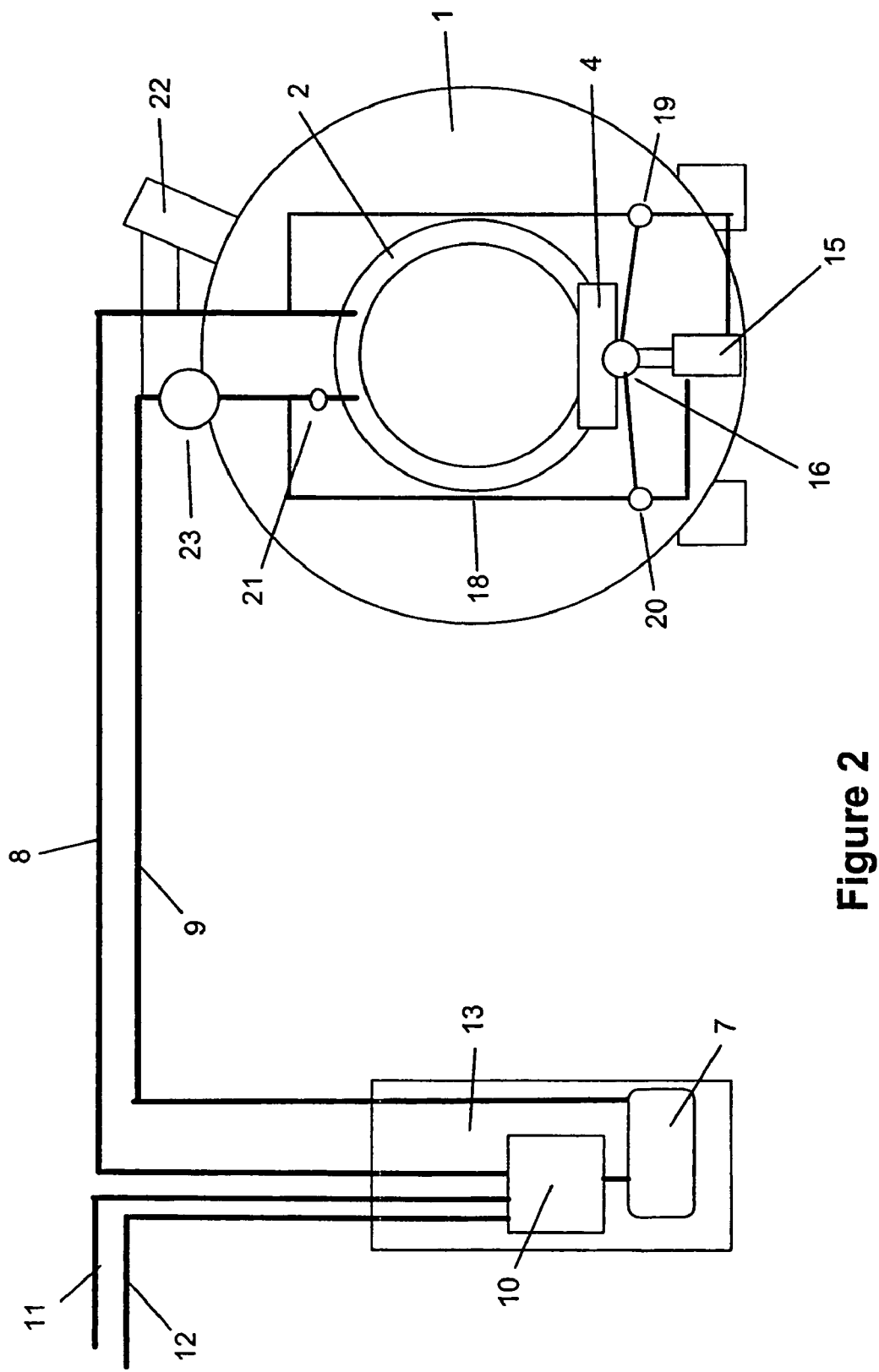
FIG. 2 shows a schematic representation of an MRI scanner according to a preferred embodiment of the invention.

Referring to FIG. 2, components that are common to FIG. 1 carry the same numerals in both figures.

In this embodiment vertical and horizontal movement of the patient table are provided by hydraulic pistons or motors 15 and 16 respectively. The fluid directed by secondary supply and return conduits 8 and 9 serves as coolant for the gradient coil 2 and as the hydraulic fluid necessary for operation of the pistons or motors 15, 16. Additional fluid conduits 17 and 18 direct the coolant/hydraulic fluid to and from pistons or motors 15 and 16, via control valves 19 and 20.

One or more shut off valves 21 may be employed to divert coolant/hydraulic fluid from the gradient coil when the hydraulic pistons 15, 16 are being operated.

Delivery and return of cryogenic refrigerant are controlled by a hydraulic valve motor 22 and patient cooling fan 23 is driven by an hydraulic motor.

Typical coolant/hydraulic fluids would include water and a water glycol mixture although other suitable fluids could be determined by routine experimentation.

The foregoing disclosure has been set forth merely to illustrate the invention and is not intended to be limiting. Since modifications of the disclosed embodiments incorporating the spirit and substance of the invention may occur to persons skilled in the art, the invention should be construed to include everything within the scope of the appended claims and equivalents thereof.

The invention claimed is:

1. Apparatus comprising:
    a patient table;
    at least one hydraulic piston or motor arranged to effect movement of the table;
    means for directing fluid to said hydraulic piston or motor, the fluid being suitable for use as a hydraulic fluid;
    means for directing the fluid to the vicinity of other components of the apparatus, the fluid also being suitable for use as a coolant;
    a Magnetic Resonance Imaging (MRI) scanner having a gradient coil, wherein the fluid is directed to the vicinity of said gradient coil; and
    means for preventing a flow of fluid to the gradient coil while the at least one hydraulic piston or motor is operated.

2. Apparatus according to claim 1, further comprising:
    a hydraulic motor adapted to drive a cooling fan; and
    means for directing the fluid to the cooling fan;
    wherein the cooling fan is arranged to deliver cooling air in the vicinity of the patient table during operation of the MRI scanner.

3. Apparatus according to claim 2, further comprising:
    a hydraulic motor arranged to drive valves controlling the delivery and return of cryogenic refrigerant; and
    means for directing the fluid to said valves.

4. A method of moving a patient table in an apparatus, said method comprising:
    engaging a hydraulic piston or motor with the table;
    directing a fluid to the hydraulic piston or motor; and
    cooling at least one other component of the apparatus by directing the fluid thereto; wherein,
    the apparatus is an MRI scanner having a gradient coil;
    cooling of the coil is effected by directing fluid thereto; and
    a flow of fluid to the gradient coil is prevented during moving of the table.

5. A method according to claim 4, further comprising diverting fluid to a hydraulic motor, and thereby driving a patient cooling fan.

6. A method according to claim 5 and further comprising diverting fluid to a hydraulic motor, and thereby operating valves to control the delivery of cryogenic refrigerant.

7. A process for upgrading an apparatus, said apparatus having a cooling system which directs coolant fluid to at least one component of the system via at least one fluid conduit and also having at least one motor to provide movement of at least one component of the system; said process comprising:
    substituting at least one motor with at least one hydraulic piston or motor;
    modifying the at least one fluid conduit such that fluid is directed to the at least one hydraulic piston or motor; and
    substituting the coolant fluid with a fluid suitable for serving as a hydraulic fluid and a coolant fluid.

* * * * *